United States Patent [19]

Cantenys

[11] Patent Number: 5,129,915
[45] Date of Patent: Jul. 14, 1992

[54] INTRAGASTRIC BALLOON

[76] Inventor: José Cantenys, 1501 Palézieux-Village, Switzerland, 1501

[21] Appl. No.: 490,576

[22] PCT Filed: May 31, 1989

[86] PCT No.: PCT/CH89/00102

§ 371 Date: Feb. 26, 1990

§ 102(e) Date: Feb. 26, 1990

[87] PCT Pub. No.: WO90/00376

PCT Pub. Date: Jan. 25, 1990

[30] Foreign Application Priority Data

Jul. 5, 1988 [CH] Switzerland ............. 2549/88

[51] Int. Cl.$^5$ ............................................. A61B 17/00
[52] U.S. Cl. ................................. 606/192; 604/96; 604/54; 128/898
[58] Field of Search ............... 604/96, 54; 606/192, 606/195; 128/898, 899

[56] References Cited

U.S. PATENT DOCUMENTS 4,485,805 12/1984 Foster, Jr. .................. 604/96 X
4,694,827 9/1987 Weiner et al. ................. 606/192
4,925,446 5/1990 Garay et al. ................... 604/96

FOREIGN PATENT DOCUMENTS 0103481 3/1984 European Pat. Off. .
0241038 10/1987 European Pat. Off. .
8700034 1/1987 World Int. Prop. O. .

Primary Examiner—Robert A. Hafer
Assistant Examiner—Kerry Owens
Attorney, Agent, or Firm—Townsend and Townsend

[57] ABSTRACT

A balloon intended to be swallowed and to occupy a given volume of the stomach in the presence of other balloons of the same type in order to permit a weight reduction of an individual is made up of an envelope containing two substances capable of reacting chemically with each other and with water in order to form a gas permitting the inflation of the balloon. The two substances are isolated by a coating melting under the effect of human body temperature. Other applications may be foreseen for a balloon capable of inflating automatically under the effect of a predetermined temperature.

12 Claims, 1 Drawing Sheet

FIG. 1
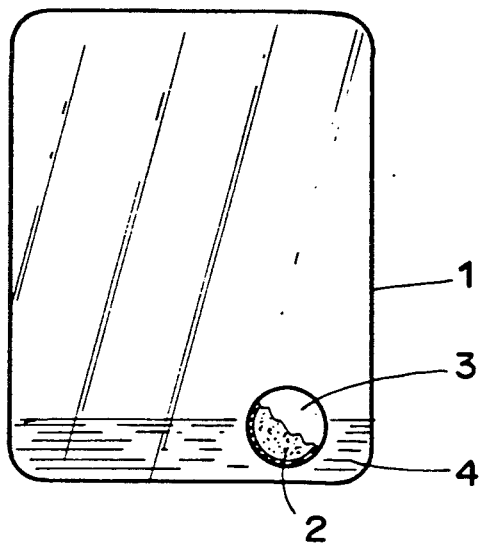
FIG. 2
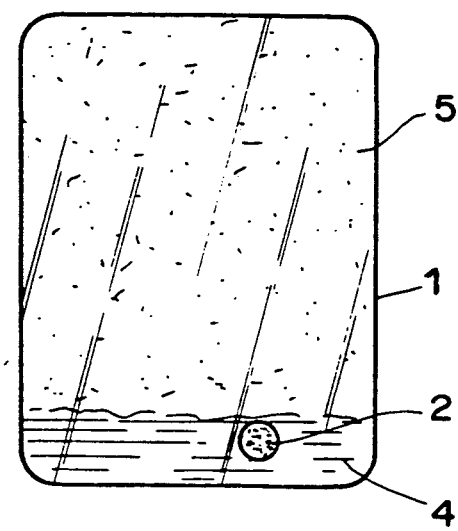
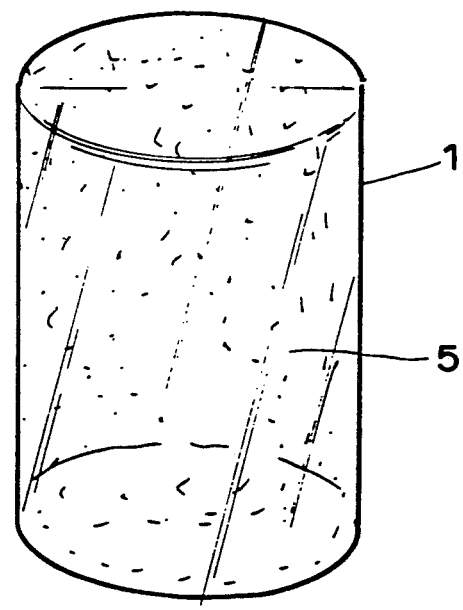
FIG. 3

INTRAGASTRIC BALLOON

Already known are intragastric balloons which, placed in the stomach of an obese person, diminish the capacity of the stomach, which has the effect of diminishing the appetite and, consequently, causes an appreciable loss of weight, this loss of weight being moreover increasable if, parallel to the treatment by intragastric balloon, the person follows a diet. However, the placement of said intragastric balloons in the person's stomach is not unproblematic. Indeed, this placement necessitates an outpatient operation, or even a one-day hospitalization, and in addition, local anesthesia of the throat is necessary at the time of introduction of the balloon; the balloon must then be inflated with the aid of compressed air, for example, so as to obtain the desired volume. The withdrawal of the balloon after a few weeks or a few months likewise necessitates an outpatient operation; in addition, regular checks, carried out by a doctor, are called for. This treatment is therefore not only exacting but is costly as well.

Another proposal has been made of a balloon inflating under the effect of a chemical reaction causing the emanation of a non-toxic gas; the components necessary for the chemical reaction are brought in contact just before the balloon is swallowed, or else the reaction is started by the action of the liquids situated in the stomach or else the components are isolated by sugar or similar material, dissolving under the action of water.

According to another proposal, the balloon is filled in the deflated state with a liquid having a low melting point turning into gas under the effect of human body temperature.

These various proposals generally have the drawback of not having control over the moment of inflation of the balloon, this inflating then occurring too soon, before the balloon is in the stomach, this being able to bring about all sorts of trouble for the person under treatment. On the other hand, the prior art mentions the use of a balloon, even of two or three simultaneously in the stomach; the use of balloons of relatively large dimensions may lead to serious drawbacks, even to intestinal occlusions.

SUMMARY OF THE INVENTION

The object of the present invention is to provide an intragastric balloon inflating without outside means within the stomach, and which, being of small size, can easily be eliminated by the natural routes when it has been deflated, and which, being present simultaneously in a large number, permits a certain volume to be occupied in a person's stomach, and which remedies the above drawbacks.

To this end, the balloon is made up of an envelope which is at least approximately fluid-tight, enclosing at least one substance or a composition which permits an inflation of the envelope within the person's stomach to be caused automatically and without bringing in outside energy, characterized in that this inflation derives from a chemical reaction made possible by the melting of the coating of one of the constituents.

BRIEF DESCRIPTION OF DRAWINGS

Other characteristics of the invention will follow from the detailed description of the subject of the invention, referring to the appended drawing in which FIG. 1 is an elevation of an embodiment of the balloon in its deflated state, FIG. 2 is an elevation of an embodiment of the balloon during the chemical reaction causing the inflation of the envelope to form the balloon, FIG. 3 is a perspective view of an embodiment of the balloon in its inflated state.

FIG. 1 shows the main elements of an embodiment of the subject of the invention, viz.:
- the envelope 1 hermetically closed by welding of its periphery, for example,
- a substance or composition 2 reacting chemically with the substance 4 in order to form a gas,
- the coating 3 isolating the substance or composition 2 from the substance 4 at a temperature lower than that of the human body.

DESCRIPTION OF PREFERRED EMBODIMENTS

In this figure, the chemical reaction not being able to take place, the balloon is deflated and can, in view of its small size, easily be swallowed with the aid of a little water, for example.

In one embodiment of the invention, the envelope 1 may be produced of flexible synthetic material such as polyethylene, polypropylene, PVC, PVCD, PET, Teflon, or any other appropriate type of material. The choice of the envelope-forming material, the thickness of the film, as well as its microporosity, will be chosen in such a way that the permeability of the envelope permits the balloon to deflate gradually after a few hours or a few days, for example; the active periods can thus be modulated according to the intensity of the cures. The balloon will therefore deflate after a certain predetermined time and will be evacuated by the natural routes. The material of the envelope will obviously be chosen so that it presents no danger of poisoning for the person. The same will apply to the substance or composition 2, to the substance 4, to the coating 3, as well as to the gas resulting from the chemical reaction. In one embodiment of the invention, the composition 2 might be a pastille or a powder comprising a solid acid and a non-toxic carbonate or bicaronate, whereas the substance 4 would be water and the coating 3 chocolate, cocoa paste or cocoa butter. It goes without saying that other embodiments, such as, for instance, citric acid and an alkaline bicarbonate coated with non-toxic vegetable or animal fat melting at human body temperature and which placed in the presence of water, would produce the same result.

FIG. 2 depicts the balloon, subject of the present invention, when it has been swallowed and is in the stomach. The coating having melted slowly under the effect of the temperature prevailing within the stomach, the composition 2 comprising, for example, citric acid and sodium bicarbonate, is going to generate $CO_2$ 5 by reacting in the presence of the water 4 and is thereby going to start to inflate the envelope with a view to forming the balloon.

FIG. 3 depicts the balloon, subject of the present invention, fully inflated by the $CO_2$. The salt resulting from the chemical reaction, as well as the melted coating, is not depicted.

In another embodiment of the invention, the mixture of components 2 is isolated from the water 4 by an isolation pouch of low-strength synthetic material which it will suffice to break immediately before swallowing the envelope.

The shape and the size of the balloon will be chosen as a function of various practical criteria, viz.: ease of swallowing the envelope, elimination of the risks of internal injuries, desired volume of the balloon, etc. A packaging may also be provided, in such a way that, prior to use, the envelope appears coated in a capsule, for example. The small size of the balloon permits elimination thereof before it is completely deflated; hence the passage of one or more balloons in the semi-deflated state in intestinal transit increases the duration of this transit, thus increasing the effectiveness of the weight-reduction treatment while avoiding the risk of an intestinal occlusion.

The treatment will consist in swallowing a chosen number of balloons, this as a function of the desired diminishing of the stomach capacity. Next, at the time of a continued treatment, each balloon evacuated by the natural routes will be replaced by a new balloon.

The diminishing of the stomach capacity causing diminishing of the person's appetite, this treatment will bring about an appreciable loss of weight.

The use of a balloon inflating automatically under the effect of the temperature may also be provided for other usages than that mentioned above; in particular, as an indicator of a temperature reached in an enclosure or by some element, where this enclosure or element can be of any kind, also apart from an application to the human or animal body, for example some mechanical element, or else one supposed to actuate some mechanism as a function of a release temperature. The choice of the component isolating the constituents capable of reacting chemically and melting at a given temperature will then have to be made taking in account the desired release temperature; to this end, the proportion of a charge of oil in a wax, for example, permits choosing the temperature at which this wax will melt. Likewise, the other characteristics of the balloon, material of the envelope, size and shape of the balloon, constituents reacting chemically and inflating gas will be chosen as a function of the desired application.

I claim:

1. Intragastric balloon intended to occupy a certain volume in a person's stomach comprising, an envelope which is substantially fluid-tight enclosing at least one substance and water, the at least one substance comprising means for chemically reacting with the water to form a gas which inflates the envelope within the person's stomach, and coating means enveloping the chemically reacting means, the coating means having a melting temperature in the range of between about 25° C. to about 35° C. so that the chemically reacting means and the water are maintained separate of each other while the temperature of the coating means is below said range, and the coating melts, permitting the mixing of the chemically reacting means and the water after a person has swallowed the envelope and the temperature of the coating means has reached said range inside the person's stomach so that said chemical reaction occurs thereafter and the gas formed by the reaction inflates the envelope inside the person's stomach.

2. Intragastric balloon according to claim 1, wherein the coating means comprises a vegetable or animal fat.

3. Intragastric balloon according to claim 1, wherein the envelope is comprised of a material selected from the group of polyethylene, polypropylene, PVC, PVCD, PET, and Teflon.

4. Intragastric balloon according to claim 1, wherein the envelope has a porosity chosen to permit deflation of the balloon after a predetermined time.

5. Intragastric balloon according to claim 1, wherein the balloon is packaged in a capsule.

6. Intragastric balloon according to claim 1, wherein a plurality of the balloons is used to occupy the necessary volume.

7. Self-inflatable balloon comprising, an envelope which is substantially fluid-tight, enclosing at least one substance and water, the at least one substance comprising a chemical substance, the chemical substance selected so that a chemical reaction occurs when the chemical substance is mixed with the water, the chemical reaction producing a gas which inflates the balloon, the at least one substance further comprising a coating having a melting temperature no higher than about 37° C., the coating enclosing the chemical substance thereby keeping the chemical substance and the water separate when the coating is solid, the coating permitting mixing of the chemical substance and the water to produce the chemical reaction when the coating becomes liquid.

8. Intragastric balloon according to claim 1, wherein the at least one substance comprises citric acid.

9. Intragastric balloon according to claim 1, wherein the at least one substance comprises sodium bicarbonate.

10. Intragastric balloon according to claim 1, wherein the gas comprises carbon dioxide.

11. Intragastric balloon intended to occupy a volume in a person's stomach comprising, an envelope which is substantially fluid-tight enclosing at least one substance and water, the at least one substance comprising a means for chemically reacting with the water to form a gas which inflates the envelope within the person's stomach, and coating means enveloping the chemically reacting means, the coating means being solid at a temperature below human body temperature and having a melting temperature of no more than about 37° C. so that the chemically reacting means and the water are maintained separate of each other while the coating is solid, and the coating means melts, permitting the mixing of the chemically reacting means and the water after a person has swallowed the envelope and the temperature of the coating means has reached said melting temperature inside the person's stomach so that the chemical reaction occurs thereafter and the gas formed by the reaction inflates the envelope inside the person's stomach.

12. Intragastric balloon intended to occupy a volume within a person's stomach comprising, an envelope which is substantially fluid-tight, the envelope enclosing at least one substance and water, the at least one substance comprising a means for chemically reacting with the water to form a gas which inflates the envelope within the person's stomach, and coating means enveloping the chemically reacting means, the coating means being selected from the group consisting of chocolate, cocoa paste, cocoa butter, vegetable fat, animal fat, and a mixture of oil and wax, the coating means being solid at a temperature below human body temperature and having a melting temperature of no more than human body temperature so that the chemically reacting means and the water are maintained separate of each other while the coating means is solid, and the coating means melts at the melting temperature permitting mixing of the chemically reacting means and the water so that the chemical reaction occurs thereafter and the gas formed by the reaction inflates the envelope inside the person's stomach.

* * * * *